US00PP17172P2

(12) United States Plant Patent
Korlipara

(10) Patent No.: US PP17,172 P2
(45) Date of Patent: Oct. 24, 2006

(54) ***ECHINACEA PURPUREA* PLANT NAMED 'GREEN EYES'**

(50) Latin Name: *Echinacea purpurea*
Varietal Denomination: Green Eyes

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/155,226

(22) Filed: Jun. 16, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell

(57) ABSTRACT

A new and distinct cultivar of *Echinacea purpurea* plant named 'Green Eyes' characterized by its unique inflorescences of deep red purple ray florets that are spread out perpendicular to the stem with lime green centers on young inflorescences, lovely fragrance, and an upright vigorous habit.

1 Drawing Sheet

Botanical denomination: *Echinacea purpurea.*
Variety designation: 'Green Eyes'.

The present invention relates to a new and distinct cultivar of *Echinacea purpurea* and given the cultivar name 'Green Eyes'. *Echinacea* is in the family Asteraceae. This new cultivar originated from an open pollinated cross between *Echinacea* 'Ruby Giant', an unpatented plant, as the seed parent, and an unknown pollen parent.

This new *Echinacea purpurea* cultivar is distinguished by:

1. Large red purple inflorescences with a double row of ray florets.
2. Ray florets spread out stiffly, parallel to ground.
3. Lime green centers when disc florets are unopened.
4. Lovely fragrance.
5. Strong upright stems.
6. Good vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a close up of the inflorescence of a one year old *Echinacea purpurea* 'Green Eyes' growing in the ground in the field in the summer in Canby, Oreg.

DETAILED PLANT DESCRIPTION

The following is a detailed description of the new *Echinacea purpurea* cultivar based on observations of a one-year-old specimen growing in the ground in full sun under typical outdoor conditions Canby is Zone 8 on the USDA Hardiness map. Temperatures range from a high of 95 degrees F. in August to 32 degrees F. in January. Normal rainfall in Canby in 42.8 inches per year in the trial fields in Canby, Oreg. The color descriptions are all based on The Royal Horticultural Society Colour Chart.

Botanical denomination: *Echinacea purpurea.*
Variety designation: 'Green Eyes'.

Plant:

*Type.*—Herbaceous perennial.
*Hardiness.*—USDA Zones 4 to 9.
*Size.*—30 cm wide and 78 cm tall to top of inflorescences.
*Form.*—Basal clump.
*Vigor.*—Excellent.
*Roots.*—Fibrous, with many downward growing and few laterals, ivory in color, Yellow White 158D. Roots develop easily from cuttings from the crown.

Leaf:

*Type.*—Simple.
*Shape.*—Ovate.
*Arrangement.*—Alternate.
*Blade size.*—8 to 15 cm long and 4.5 to 7 cm wide at the widest part.
*Margins.*—Serrate.
*Apex.*—Acuminate.
*Base.*—Attenuate, continuing down petiole.
*Texture.*—Like sandpaper.
*Surface texture.*—Strigose.
*Venation.*—Pinnate, with three main veins from near the base.
*Color.*—Topside — Deep Green, Closest to Yellow Green 147A, but darker. Bottom — Yellow Green 147B.
*Petiole length.*—16.5 cm if basal leaf, 1 to 1.5 cm if cauline leaf and 4 mm wide on both.
*Petiole surface texture.*—Strigose.
*Petiole color.*—Yellow Green 147B.

Peduncle:

*Height.*—78 cm.
*Diameter.*—6 mm near flower head.
*Surface texture.*—Strigose.

*Color.*—Yellow Green 146C speckled or mottled with Greyed Orange 177A.

Inflorescence:

*Type.*—Long stalked terminal heads, perfect, zygomorphic.

*Size.*—12.5 cm wide and 2 to 5 cm deep as disc enlarges.

*Ray florets.*—In 2 series, usually between 28 and 35 florets, with entire margins. Shape: Oblanceolate with the tip occasionally two toothed. Size: 5.7 cm long, 1.3 cm wide. Texture — Rubbery. Surface texture — Glabrous.

*Disc.*—Shape—Convex becoming conic. Size—4.5 to 4.8 cm wide and becoming 3.5 cm deep with maturity. Floret from the side—10 mm long, Yellow Green 145B, 5 lobed, each floret with one persistent, very stiff bract, 12 mm long, which gives the disc color. Pistil — 7 mm long, extruding, 2-branched stigma, Greyed Purple 187A. Stamen number —5. Pollen color — Yellow Orange 19A.

*Color.*—Ray floret, topside — Red Purple 71B. Ray floret, bottom side — Red Purple 70A. Disc floret as seen from the top — Yellow Green 144A when in bud, change to orange, Yellow Orange 28B tipped with Greyed Red 179A then mature to Greyed Purple 187A.

*Phyllaries* (*at the base of each head*).—Phyllaries in four leafy series, lobes lanceolate in shape, reflexed, apex acute, margins entire, strigose on back side and glabrous on inside, in an area of 3.5 to 5 cm wide.

*Phyllary size.*—Grows to 17 mm long and 3 mm wide.

*Phyllary color.*—Yellow Green 147A on both sides.

*Bloom period.*—July through September in Canby, Oreg.

*Fragrance.*—Lovely, strong.

Seed: Not Seen.

*Fertility.*—Fertile.

Disease and pests: *Echinacea* are susceptible to leaf miners, powdery mildew, bacterial spots, and gray mold. None of these have been observed on plants grown under commercial conditions in Canby, Oreg.

COMPARISONS TO SIMILAR *ECHINACEA*

Compared to *Echinacea purpurea* 'Ruby Giant' and 'Magnus', unpatented plants, the ray florets of this new cultivar are deeper red purple and the young disc florets are a distinctive lime green, rather than orange.

I claim:

1. A new and distinct cultivar of *Echinacea purpurea* plant as herein illustrated and described.

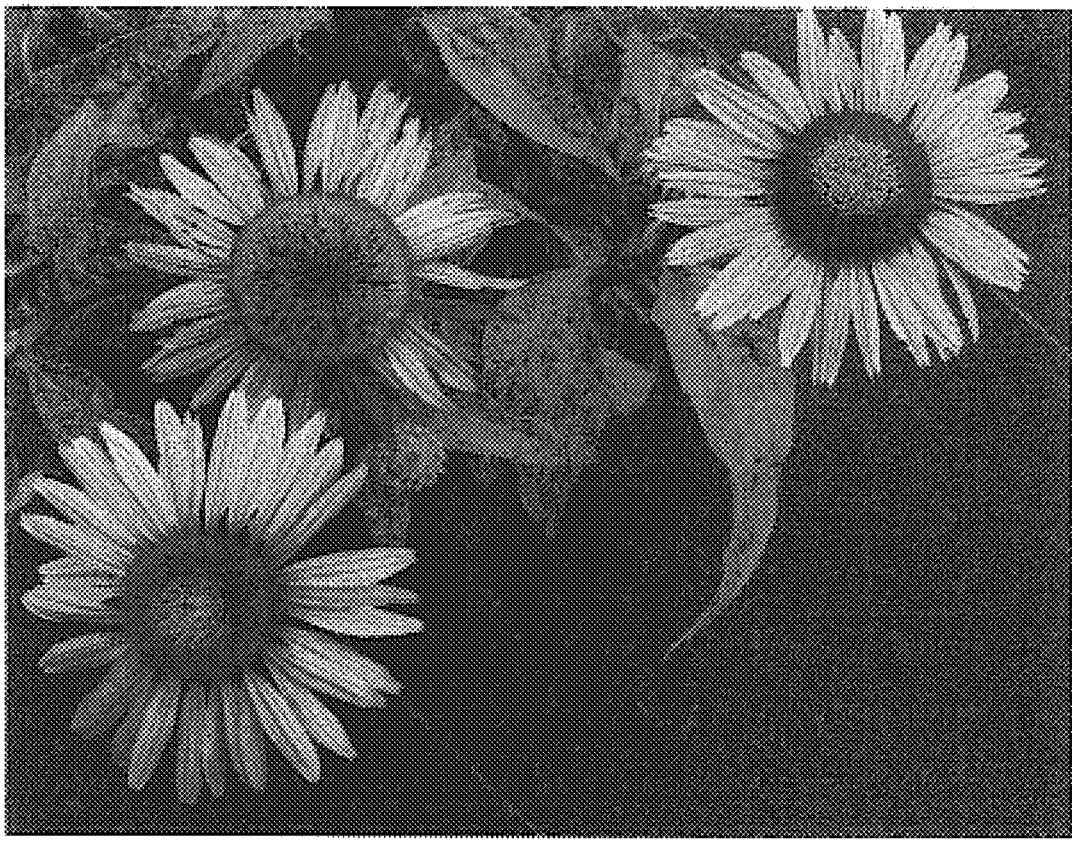

* * * * *